United States Patent [19]

Bates et al.

[11] Patent Number: 4,562,834

[45] Date of Patent: Jan. 7, 1986

[54] WATERPROOF LIMB COVERING

[76] Inventors: Norman Bates, 194 Fenn Ave., Willowdale, Ontario, Canada, M2P 1Y1; Carl M. Naumoff, 169 Hammersmith Ave., Toronto, Ontario, Canada, M4E 2W7

[21] Appl. No.: 560,480

[22] Filed: Dec. 12, 1983

[51] Int. Cl.$^4$ .............................................. A61F 13/00
[52] U.S. Cl. ...................................... 128/82; 128/157
[58] Field of Search .................... 128/82, 83, 157, 165

[56] References Cited

U.S. PATENT DOCUMENTS

| | | | |
|---|---|---|---|
| 3,741,203 | 6/1973 | Liman | 128/82 |
| 3,747,125 | 7/1973 | Goldman et al. | 128/82 |
| 4,254,765 | 3/1981 | Brown et al. | 128/82 |

*Primary Examiner*—John D. Yasko
*Attorney, Agent, or Firm*—Rogers, Bereskin & Parr

[57] ABSTRACT

A waterproof covering intended to be worn over a cast or bandage on an injured arm or leg. The covering comprises a generally tubular water impervious sleeve which is closed at one end and which has spaced cutting sites running from side to side along which the sleeve can be cut to different lengths. Apertured tabs are provided along the length of the covering to receive a strap for encircling the covering and sealing the covering around the limb, when the covering is cut at the cutting sites. Visual indicators identify the cutting sites. Additional seam segments serve to provide resistance to tearing at side edges.

14 Claims, 8 Drawing Figures

WATERPROOF LIMB COVERING

This invention relates generally to waterproof coverings for human limbs and is concerned more particularly with a covering which is capable of being worn over a cast or bandage on an arm or leg.

Waterproof cast and bandage coverings have previously been proposed as an aid to permitting a person having a cast or bandage to bathe and shower with minimum risk of sustaining water damage to the cast or bandage, skin irritation or further injury. In a simple form, a waterproof covering can be improvised from a plastic garbage or grocery bag taped or tied around the cast or bandage, or secured using a common elastic band. This type of covering has several disadvantages including the difficulty of effectively and neatly sealing the bag around the cast or bandage. Commercial garbage or grocery bags of polyethylene often do not have completely waterproof seams. Also, the bags often have unsuitable length and width dimensions, as well as having smooth and slippery surfaces which can become a hazard in the shower. Common elastic bands are usually narrow and concentrate their forces on a small area of the limb when applied, and can cause discomfort. Generally common elastic bands secure the bag to the limb below the upper marginal edge of the bag leaving the upper open end of the bag exposed to water entry. Water will travel from the area above the seal area to the area below the elastic band seal area along folds in the skin and plastic bag which will act as water pathways.

Specially designed cast and bandage covers have also been proposed but also have various disadvantages. One commercial product is sold under the Canadian trade mark CAST GUARD and is said to be fabricated from surgical grade latex by a blow moulding technique. Another commercial product is sold under the name "DRY SPELL WATERPROOF LEG AND ARM GUARD" and is manufactured by Dry Spell Industries of New York, U.S.A. A disadvantage common to both of these products is that they are available in fixed sizes only. Where the manufacturer makes available a range of sizes, the retailer must carry a relatively large stock or, where different sizes are not available, the user may be forced to wear a covering which is poor-fitting, and or less effective. Not only can this be inconvenient and uncomfortable but there can be a safety hazard in terms of the possibility of the wearer slipping or tripping over a covering which is too large. Fixed size protective coverings do not provide for size reduction as may be required when for example a full length cast is replaced with a shorter version as healing progresses.

The United States Patent literature also discloses several examples of prior art protective coverings of the general type in question. For example, U.S. Pat. No. 4,254,765 (Brown) discloses a protective covering in the form of a sleeve of fixed size, having an elongated closure strap fastened to the sleeve. Becausse of the fastened straps, this design does not allow sizing adjustments. Similarly, U.S. Pat. Nos. 2,244,871 and 4,346,699 disclose non-adjustable limb coverings. A heat shrinkable plastic sleeve is disclosed in U.S. Pat. No. 3,329,143 (Gordon). Other examples of prior art devices considered during the preparation of this application are disclosed in the following U.S. Pat. Nos.:
  3,416,518 (Samuels)
  3,657,741 (Blanco)
  3,906,941 (Cook)
  4,224,935 (Metelnick)

An object of the present invention is to provide a covering of the general type referred to above, which is adaptable to and equally effective for a wide range of size requirements, and changing size requirements.

The limb covering provided by the invention comprises a tubular sleeve which is made of a flexible waterproof material and which has an open top end for receiving a limb and closed bottom end. The sleeve is adapted to be laid in a flat configuration in which opposite side edges are defined longitudinally of the sleeve. The sleeve has a plurality of cutting sites which are spaced along the sleeve between the side edges at which the covering can be cut to one of a plurality of different lengths. Adjacent each cutting site is a table projecting from the relevant side edge for co-operation with a strap adapted to encircle and seal the sleeve about the limb after the sleeve has been cut to length at the cutting site.

The cutting sites may be more clearly defined when marked by seam segments proximal to the relevant side edges. Such additional seam segments also serve as to provide additional resistance to separation or tearing of the sleeve after the covering has been cut at the cutting site. In an additional embodiment, cutting sites can be more clearly and exactly identified when lines are printed between relevant side edges along the length of the cutting site.

The protective covering provided by the invention has the advantage that it can be fitted snugly to any injured limb by measuring the sleeve against the limb and then simply cutting along the appropriate one of the cut sites as indicated. The combination of the integral tabs and the straps allows for secure and facile fastening and sealing of the covering to the limb. Preferably, the strap is elastic and can be fitted around the sleeve and limb with only one hand as facilitated by the attachment of the strap to the covering. The simple one-handed assembly of the article allows a person with an arm injury to use the device unaided. Furthermore, if a clear vinyl or other plastic material is used for the sleeve, it is possible to visually detect water leakage.

In order that the invention may be more clearly understood, reference will now be made to the accompanying drawings which illustrate preferred embodiments of the invention by way of example. In the drawings.

Figure 2:
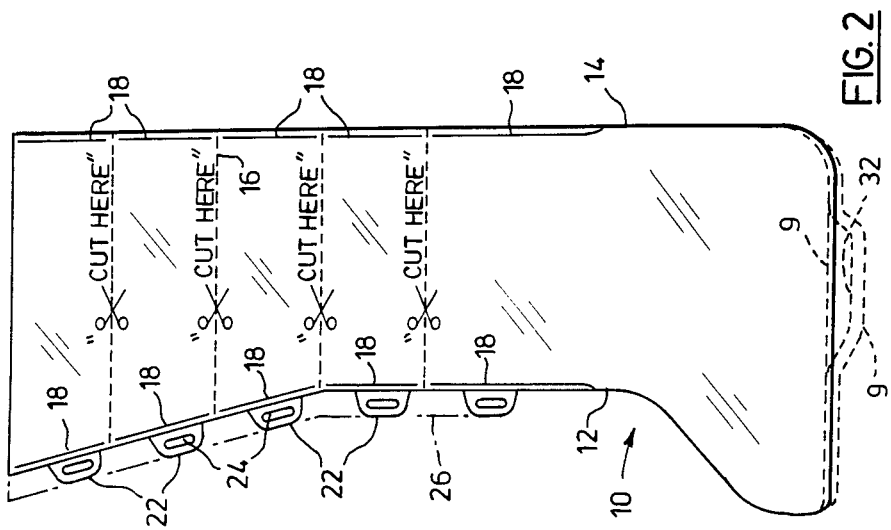
FIG. 2 is a front elevational view of another form of covering for use on a leg or foot.

FIG. 3 (*a*), (*b*) and (*c*) are perspective views illustrating sequential steps in securing the covering of FIG. 2 about a leg;

FIG. 4(*a*), (*b*) and (*c*) are partial front elevational views illustrating how one form of elastic strap may be coupled to the protective covering.

Figure 1:
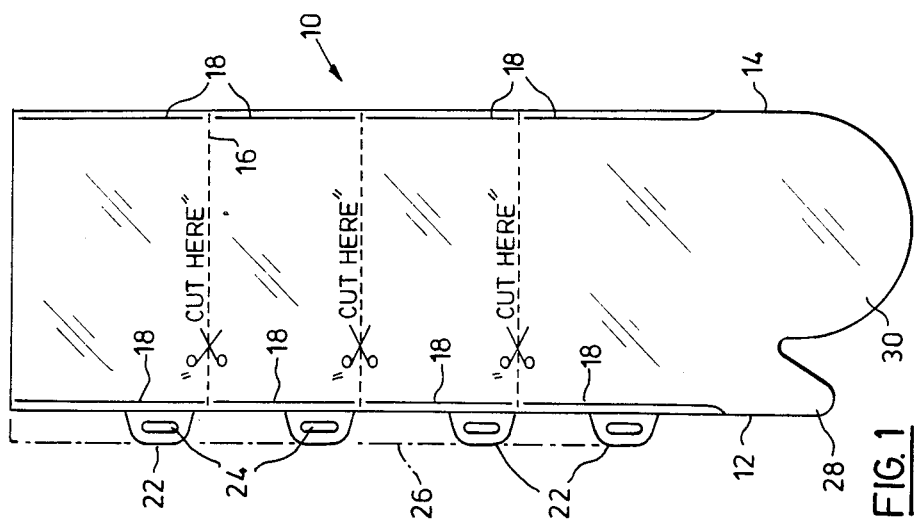
FIG. 1 is a front elevational view of one form of protective covering designed to be used on arm or a hand.

Referring first to FIGS. 1 and 2, the coverings shown in those views are designed respectively as a full length arm and leg model and will in fact be the only models which a retailer will have to stock. The two models are constructed in essentially the same fashion but are differently shaped. In each case, the covering comprises a generally tubular sleeve of a clear water impervious material (e.g. vinyl 0.6 mm to 1.2 mm thickness or polyethylene 0.6 mm thickness). Vinyl material of 0.6 to 1.2 mm thickness has been found to be strong and water impervious as well as puncture and tear resistant.

In each case (FIGS. 1 and 2) the sleeve is made up of two separate sheets of material sealed together along two sides and one edge to form a watertight bag. This allows the sleeve to be laid in a flat configuration with the two sheets forming superimposed layers and the covering is in fact shown in this configuration in FIGS. 1 and 2. In an alternative embodiment, the sleeve could of course be formed by one sheet of material folded over to form the two layers. In any event, in the illustrated embodiment, the two sheets of material are sealed together by high frequency welding or heat sealing in the configurations shown. Again, in alternative embodiments, other sealing techniques could be used (e.g. sewing or gluing). Alternatively, blow moulding techniques or injection moulding techniques could be used to make the covering.

The coverings shown respectively in FIGS. 1 and 2 are essentially the same but of different shapes. Similar reference numerals will therefore be used to denote corresponding parts in the two views. The covering itself is denoted by reference numeral 10 and, as indicated above, is shown laid in a flat configuration in which opposite side edges 12 and 14 are defined longitudinally of the sleeve. The sleeve is provided with a plurality of cutting sites or locations 16 which are spaced along the sleeve and extend between the side edges 12 and 14. The cutting sites are defined by seam segments 18 on each side 12 and 14 of the covering, and printed lines extending between the side edges 12 and 14. By way of example, the covering shown in FIG. 1 may be of an overall length of approximately 33 inches with the cutting sites 16 spaced at 4 inch intervals from one another. The overall width of the sleeve as laid flat may be approximately 11 inches. In the case of the leg covering shown in FIG. 2, the overall length may be approximately 44 inches with cutting locations spaced at approximately 4 inch intervals. The maximum width of the covering may be approximatley 17 inches reducing to a minimum of 14 inches in the ankle area.

Seam segments 18 are formed by heat sealing or welding together opposite surfaces of the sleeve to form what will be known as "rip stop welds".

Tabs 22, each having an opening 24, protrude integrally from the side of the covering adjacent each cutting site 16. Each tab is closer to the closed end of the covering than the associated cutting site 16, e.g. by about one inch. In an alternative embodiment, the tabs can be formed by portions of a continuous flap down the entire side of the covering, as indicated in ghost outline at 26. In a further alternative embodiment, tabs may not have openings but may be provided simply as flaps onto which the member strap is fastened using a pinching device. In other embodiments apertured or non-apertured tabs may be provided on either or both side edges of the sleeve.

The covering shown in FIG. 1 has a thumb compartment 28 and forefinger compartment 30 at the closed end of the sleeve for receiving a hand. In FIG. 2, the closed end of the sleeve is shaped to receive a foot.

It should be noted that in the FIG. 2 embodiment, the tab side 12 of the covering tapers outwardly from the middle upward, so that the width of the covering increases above the mid-length area in order to conform with the general anatomical shape of the leg. It should also be noted however in FIG. 2 that the covering may also be tube shaped with generally parallel side edges, such as illustrated in FIG. 1.

In FIG. 2, refrence numeral 9 indicates that the lower (sole) surface of the covering can be provided with a non-slip surface, and the dotted outline 32 represents an optical rounded heel formation.

Figure 3C:
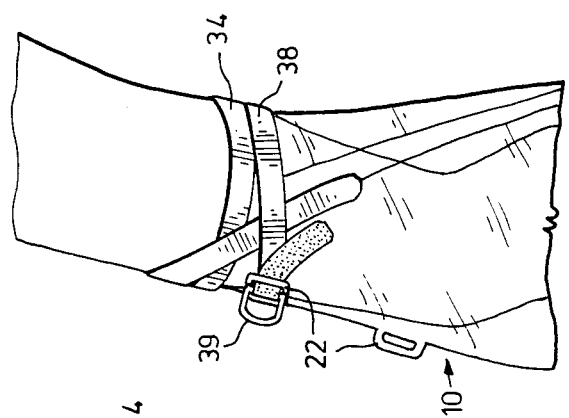
Figure 3B:
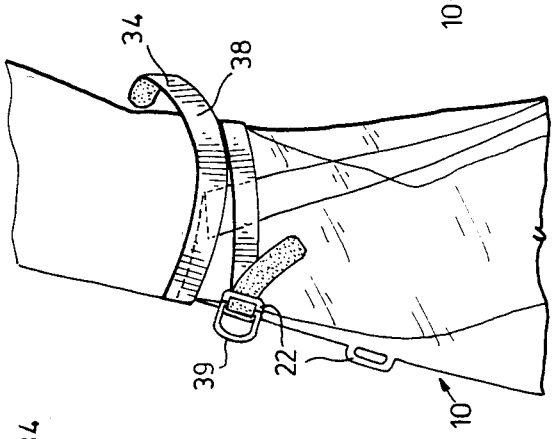
Figure 3A:
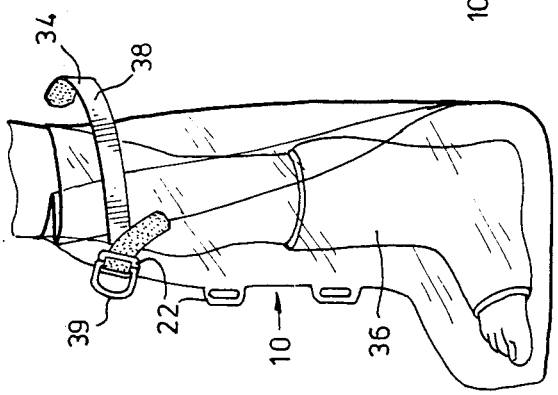

FIGS. 3(a) to (c) show the leg covering of FIG. 2 in use with an elastic strap member 34 encircling and sealing the covering around the limb to provide a closed water-roof environment for a cast 36 on a wearer's leg. The covering has previously been cut to length an appropriate distance above the cast 36 (e.g. 2 to 4 inches). The strap member is then coupled at one end to the tab 22 nearest the open upper end of the covering (see later) and the strap member then is wrapped around the upper marginal portion of the covering below and above the cutting location at least one complete turn. FIGS. 3(a) and (b) illustrate these steps. The outer end portion of the strap member is then tucked down below the section of the member nearest the tab (FIG. 3(c)) and retained by friction. An arm covering would of course be retained in similar fashion.

Figure 4C:
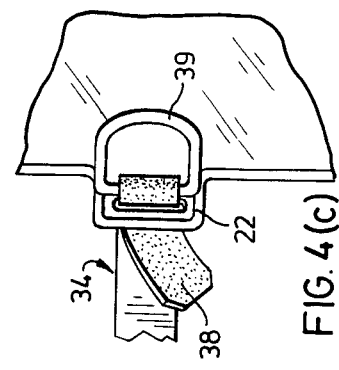
Figure 4B:
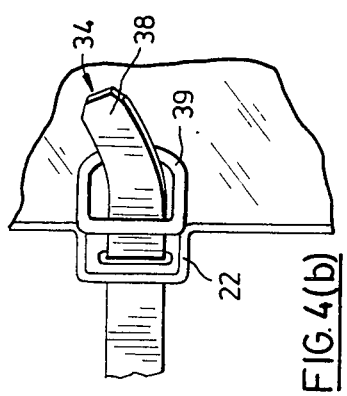
Figure 4A:
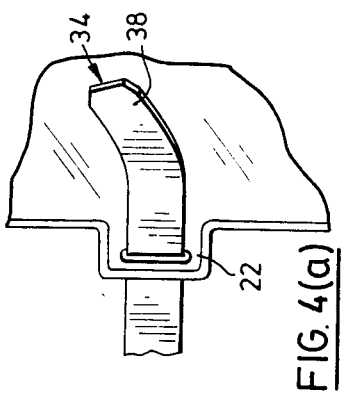

FIGS. 4(a) and 4(b) and 4(c) illustrate the manner in which the strap member 34 is attached to the covering. The strap member comprises a narrow rectangular band 38 of neoprene closed-cell spong rubber. The strap member 34 is coupled to the tab 22 of the covering by; inserting one end 38 of the strap member 34 through the opening 24 of the tab (FIG. 4(a)), then inserting the same strap member end 38 through a strap coupling device 39 (FIG. 4(b)) in the form of a D-shaped ring; finally the strap member end 38 is reinserted back through the opening 24 in the tab 22 (FIG. 4(c)). The device 39 acts to prevent strap pull out through the tab. Length adjustments to the strap member are provided by the location on the strap member at which it is coupled to the tab.

The fact that the strap member 34 is made of neoprene closed-cell rubber material (comparable to wet suit material) not only gives elasticity to the strap and allows it to be retained securely about a limb without imposing undue localized pressure points on the limb, but also the surface characteristics of the band are such that the band will tend to "cling" to itself for added security in fastening about a limb. The neoprene strap can be stretched and wrapped about the skin without causing formation of ridges or folds on the skin surface. A strap member composed of neoprene closed cell spong material in approximately 1/16" thickenss and approximately 1⅛" in width is very elastic and as such provides a great deal of tension control and range of tightness that it can be wrapped around the limb. A smooth skin-like surface on the neoprene strap member outside surface contributes to the strength of the strap member, and a nonskin, rough under-surface aids the frictional retention characteristics of the strap member. The strength of the neoprene strap member is such that breakage will occur when excessive pulling forces are used. This will tend to reduce the possibility of a tourniquet effect from occurring around the limb when the strap member is wrapped with excessive tension around the limb. This will also protect the tab from excessive pulling forces which could cause tab breakage. The sprong-like characteristics of the neoprene strap member contribute to an effective water seal, when the strap member is compressed into the skin irregularities and cracks such as occur when the strap member is wrapped in an over-lapping manner on top of itself. The neoprene strap member is provided in lengths long enough to be wrapped several times in an overlapping manner around the limb. The neoprene strap member is narrow enough in width to be inserted into the tab aperture, and can be pulled at its end without causing uneven pulling forces to occur across the width of the band which will contribute to breakage.

While preferred forms of strap member attachment have been disclosed, it will of course be understood that the other forms of coupling devices can be used for securing the strap member to the covering. Also, in cases where complete watertightness is not required (for example if the covering is to be worn simply to keep a cast or bandage clean) the strap element can at least temporarily be dispensed with completely and the covering secured in place, for example, by tape, a tie string or other retaining means.

In any event, it will be understood that the covering provided by the invention has a number of significant advantages as compared with the prior art. The primary advantage is that the covering is adaptable to a wide range of user size requirements. As described above, the covering is designed and constructed to be cut to length by cutting off and removing the covering materials beyond the required length, preferably by cutting across at one of the cutting locations. Visual reference points aid in cutting between side edges. Additional seams serve to provide additional resistance to tearing at side edges. The strap members described are sufficiently elastic and of a length capable of effectively covering limbs of widely differing circumferences. Tabs provide for attachment of strap member to the covering. Attachment of the strap member to the covering facilitates use of the product unaided when use of one hand or arm is impaired. Neoprene closed-cell sponge material strap member serves to provide an effective seal as well as providing protection against a tourniquet effect occurring on the limb.

It should also be appreciated that the preceding description relates to a particular preferred embodiment of the invention only and that many modifications are possible within the broad scope of the invention. For example, the specific materials and dimensions referred to may of course vary. When intended for several reuses the covering itself is preferably made of a material which is relatively tough and durable and also puncture and tear resistant. When intended for single-use, a less durable material such as polyethylene may be used. Preferably, the material should be clear or at least translucent to facilitate co-ordination between the hand and eye of the user and also allow for the covering to be visually checked for water leakage. However, within the broad scope of the invention, the covering could be made of an opaque material. The sites are which the sleeve can be cut to length (e.g. site 16) need not be marked on the sleeve; for example, they may merely be indicated, e.g. by the location of the tabs.

We claim:

1. A limb covering, comprising a generally tubular sleeve which is made of a flexible waterproof material and which has an open top end for receiving said limb and a closed bottom end, the sleeve being adapted to be laid in a flat configuration in which opposite side edges are defined longitudinally of the sleeve, the sleeve being provided with a plurality of cutting sites spaced along the sleeve and extending between said side edges at which the covering can be cut to one of a plurality of different lengths, the sleeve having adjacent each cutting site a tab which projects from the sleeve and which is adapted to co-operate with a strap to encircle and seal the sleeve about the limb after the sleeve has been cut to length along at a said cutting site.

2. The combination of the covering claimed in claim 1 and a said strap, wherein the said strap is generally of narrow elongate shape dimensioned to be received in an opening in a said tab and comprises a flexible resilient waterproof material.

3. The combination as claimed in claim 2, wherein said strap is made of neoprene sponge material.

4. The combination as claimed in claim 2, wherein said strap is provided with a strap coupling device adapted to permit a portion of the strap member to be folded therearound and to then act as a catch to resist the strap member from disengaging from a said tab of the covering.

5. A covering as claimed in claim 1, wherein the closed end of the sleeve has a sock-shaped compartment.

6. A covering as claimed in claim 1, wherein the closed end defines the shape of a glove.

7. A covering as claimed in claim 1, wherein said tabs are formed by portions of a continuous tab formation extending along substantially the length of the relevant side edge of the sleeve.

8. A covering as claimed in claim 1, wherein the cutting sites traverse the sleeve and are generally parallel with each other.

9. The protective covering as claimed in claim 1, wherein the sleeve comprises a clear vinyl material.

10. The protective covering as claimed in claim 1, wherein the sleeve comprises a clear polyethylene material.

11. The protective covering as claimed in claim 1, further comprising additional side edge seams adapted to serve as visual cutting site indicators and to resist tearing of the sleeve along the relevant side edge.

12. The protective covering as claimed in claim 1, further comprising printed lines extending between said side edges to serve as cutting guides at said cutting sites.

13. The protective covering as claimed in claim 4, wherein the strap member coupling device has an integral formation to pinch and hold the outer strap member when passed through it.

14. The protective covering as claimed in claim 1, wherein said tabs are unapertured and are formed by portions of a continuous tab formation extending along substantially the length of the relevant side edge of the sleeve.

* * * * *